United States Patent [19]

Lew

[11] Patent Number: 4,941,361
[45] Date of Patent: Jul. 17, 1990

[54] THREE-IN-ONE FLOWMETER

[76] Inventor: Hyok S. Lew, 7890 Oak St., Arvada, Colo. 80005

[21] Appl. No.: 208,739

[22] Filed: Jun. 20, 1988

[51] Int. Cl.$^5$ .............................................. G01F 1/32
[52] U.S. Cl. ................................. 73/861.24; 73/195; 73/861.02
[58] Field of Search ..................... 73/195, 197, 861.02, 73/861.03, 861.22, 861.24, 203

[56] References Cited

U.S. PATENT DOCUMENTS

| | | | |
|---|---|---|---|
| 1,305,803 | 6/1919 | Irwin | 73/861.02 |
| 3,776,033 | 12/1973 | Herzl | 73/861.22 |
| 3,991,613 | 11/1976 | Adler et al. | 73/861.22 |
| 4,010,645 | 3/1977 | Hertzl | 73/861.03 |
| 4,048,854 | 9/1977 | Herzl | 73/861.02 |
| 4,523,477 | 6/1985 | Miller | 73/861.02 |
| 4,561,310 | 12/1985 | Barnard et al. | 73/861.02 |
| 4,727,756 | 3/1988 | Lew | 73/861.24 |

FOREIGN PATENT DOCUMENTS

| | | |
|---|---|---|
| 55-48612 | 4/1980 | Japan . |
| 57-173721 | 10/1982 | Japan . |
| 58-201026 | 11/1983 | Japan . |
| 830449 | 3/1960 | United Kingdom . |
| 1086628 | 10/1967 | United Kingdom . |

Primary Examiner—Herbert Goldstein

[57] ABSTRACT

The flowmeter comprising a first flow passage with a fixed cross section geometry and a second flow passage with a variable cross section geometry measures the volume and mass rates of fluid flow through the flowmeter as well as the density of the fluid. The variable cross section geometry of the second flow passage varies as a function of the dynamic pressure of the fluid flow and the difference in the volume or mass rate of the fluid flow between the two flow passages varies as a function of the variable cross section geometry of the second flow passasge. The volume or mass rates of the fluid flow through the two flow passages are measured and the dynamic pressure of the fluid flow is determined therefrom, whereupon the volume and mass flow rates of the fluid flow and the density of the fluid are determined from the data on the volume flow and the dynamic pressure, or from the data on the mass flow and the dynamic pressure.

14 Claims, 2 Drawing Sheets

THREE-IN-ONE FLOWMETER

BACKGROUND OF THE INVENTION

The present day flow measurement technology employs a volume flowmeter to measure the volume rate of flow, a mass flowmeter to measure the mass rate of flow, and a density meter to measure the density of fluid. The economic models of flowmeters and density meters are not acceptable in many applications requiring accurate measurements as the accuracy and reliability of the economic models are usually very poor. The high quality models of the instruments are quite expensive and, consequently, it is not desirable in terms of economy to purchase many single function instruments to measure different flow variables such as the volume flow, mass flow and the fluid density. In todays chemical, mineral, food and pharmaceutical processing industries, there is a very strong demand for multifunction instruments, which measure more than one flow variable in an accurate and reliable manner.

BRIEF SUMMARY OF THE INVENTION

The primary object of the present invention is to provide a three-in-one flowmeter that measures volume and mass rates of fluid flow as well as the fluid density.

Another object is to provide a multi-function flowmeter comprising a first flow passage with a fixed cross section geometry including a means for measuring the velocity of fluid moving therethrough, and a second flow passage with a variable cross section geometry including another means for measuring the velocity of fluid moving therethrough, wherein the variable cross section geometry of the second flow passage varies as a function of the dynamic pressure of fluid flow, which dynamic pressure is determined from the two values of the fluid velocity respectively measured by the two velocity measuring means.

A further object is to provide a multifunction flowmeter comprising a first flow passage with a fixed cross section geometry including a means for measuring the mass flow rate of fluid moving therethrough, and a second flow passage with a variable cross section geometry including another means for measuring the mass flow rate of fluid moving therethrough, wherein the variable cross section geometry of the second flow passage varies as a function of the dynamic pressure of fluid flow, which dynamic pressure is determined from the two values of the mass flow rates respectively measured by the two mass flow rate measuring means.

Yet another object is to provide a multifunction flowmeter including a first flow passage with a fixed cross section geometry and a second flow passage with a variable cross section geometry, wherein the variable cross section geometry of the second flow passage is provided by a fluid dynamic body pivotably or shiftably supported in a spring biased or gravity biased arrangement, which fluid dynamic body blocks the second flow passage in varying degrees as a function of the dynamic pressure of fluid flow.

Yet a further object is to provide a multi-function flowmeter comprising two sets of vortex generator-sensor combinations for measuring the velocity of fluid respectively moving through the two flow passages.

Still another object is to provide a multi-function flowmeter comprising two turbines or paddles for measuring the velocity of fluid respectively moving through the two flow passages.

Still a further object is to provide a multi-function flowmeter comprising two sets of thermal probes for measuring the mass flow rates of fluid respectively moving through the two flow passages.

Yet still another object is to provide a combination of four thermal probes that measures the mass flow rate of fluid flowing thereby.

These and other objects of the present invention will become clear as the description thereof progresses.

BRIEF DESCRIPTION OF THE FIGURES

The present invention may be described with a great clarity and specificity by referring to the following figures.

DESCRIPTION OF THE ILLUSTRATED EMBODIMENTS

Figures 1, 2:
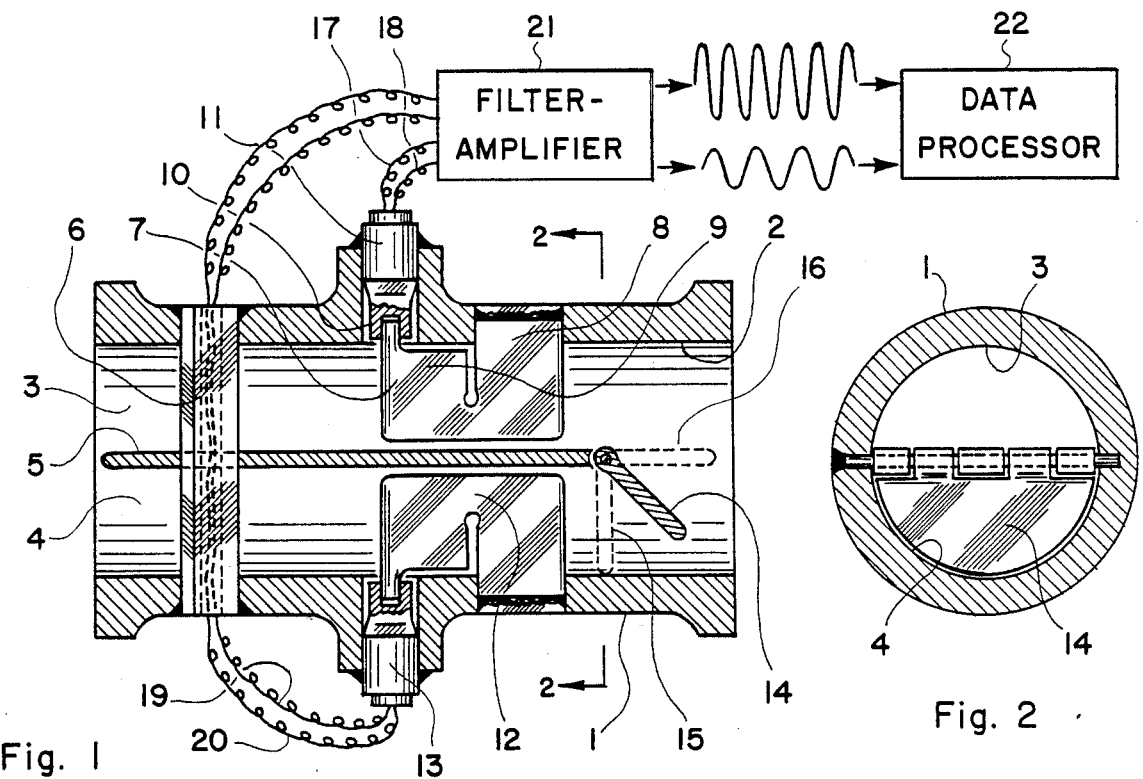
FIG. 1 illustrates a cross section of an embodiment of the present invention, that comprises two vortex generator-sensor combinations and a pivotably supported flap blocking one of the two flow passages in a spring biased or gravity biased arrangement.
FIG. 2 illustrates another cross section of the embodiment shown in FIG. 1.
Figures 3, 4, 5:
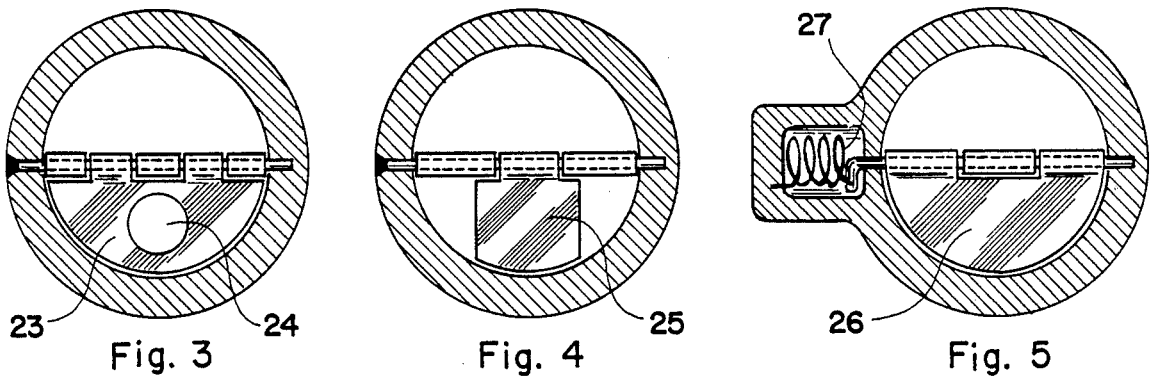
FIG. 3 illustrates a cross section of another embodiment equivalent to that shown in FIG. 2.
FIG. 4 illustrates a cross section of a further embodiment equivalent to that shown in FIG. 2.
FIG. 5 illustrates a cross section of yet another embodiment equivalent to that shown in FIG. 2.

In FIG. 1 there is illustrated a cross section of an embodiment of the multi-function flowmeter of the present invention. The body 1 of the flowmeter comprises a bore 2 that is divided into two flow passages 3 and 4 by a divider plate 5 disposed on a plane including the central axis of the bore 2. A vortex generating bluff body 6 of an elongated cylindrical shape having a blunt upstream face is disposed across a first cross section of the bore 1, which bluff body 6 anchored to the flowmeter body 1 at both extremities thereof extends through the divider plate 5. The first flow passage 3 includes a vortex sensing planar member 7 disposed across a second cross section of the bore generally parallel to the bluff body 6 on a plane parallel to the central axis of the bore 3, wherein it extends from the wall of the first flow passage 3 in a cantilever arrangement. The downstream portion 8 of one extremity of the planar member adjacent to the wall of the flow passage 3 is secured to the flowmeter body 1, while the upstream portion 9 of that extremity is connected to a force receiving member 10 of the transducer 11 that converts impulses exerted onto the force receiving member 10 into electric signals. The second flow passage 4 includes a vortex sensing planar member 12 disposed in a mirror image to the planar member 7 about the divider plate 5 and connected to the transducer 13 in the same arrangement as the combination of the planar member 7 and the transducer 11. The second flow passage 4 is blocked by a flap 14 pivotably supported by the divider plate 5, which flap is kept at the fully closed position shown by the outline thereof drawn in broken lines 15 by means of a gravity biased arrangement as shown in FIG. 2 or by means of a spring biased arrangement as shown in FIG. 5. The dynamic pressure of the moving fluid pushes the flap 14 to open positions of varying degrees. When the dynamic pressure of the fluid reaches very large values, the flap 14 is pushed to a position 16 where it lines up with the divider plate 5. The electrical wires 17 and 18 extending from the transducer 11 and the electrical wires 19 and 20 extending from the transducer 13, which may be routed through a hole axially disposed through the bluff body 6, are connected to a filter-amplifier 21, which provides data on the two vortex shedding frequencies respectively measured by the vortex sensor planar members 7 and 12 to the data processor 22 that determines the volume and mass flow rates of the fluid moving through the two flow passages as well as the density of fluid.

In FIG. 2, there is illustrated another cross section of the embodiment shown in FIG. 1, which cross section taken along plane 22 as shown in FIG. 1, shows the flap 14 at the fully closed position, which flap is kept at fully closed position in the absence of the fluid dynamic force thereon by the weight of the flap or by a spring force provided by a spring bias such as that shown in FIG. 5.

It can be shown by performing the dimensional analysis applied to the fluid flow through the flowmeter shown in FIGS. 1 and 2 that the ratio of the velocities $U_1$ and $U_2$ of the fluid respectively moving through the flow passages 3 and 4 is given by an equation of the following form:

$$\frac{U_2}{U_1} = \frac{\rho}{F}(AU_1^2 + BU_1U_2 + CU_2^2), \quad (1)$$

where $\rho$ is the density of the fluid, F is the force closing the flap 14 resulting from the weight of the flap or spring bias; A, B and C are coefficients which are functions of the velocity ratio $U_2/U_1$. The fluid velocity is proportional to the vortex shedding frequency f measured by the vortex detector, i.e., $$U_i = K_i f_i, \quad i = 1 \text{ or } 2. \quad (2)$$

Substitution of equation (2) into (1) yields the equation $$\frac{f_2}{f_1} = \frac{\rho U_1^2}{F}\left[A + B\left(\frac{f_2}{f_1}\right) + C\left(\frac{f_2}{f_1}\right)^2\right], \quad (3)$$

which can be rearranged into the form $$\frac{1}{2}\rho U_1^2 = \frac{F}{2}\left(\frac{f_2}{f_1}\right)/\left[A + B\left(\frac{f_2}{f_1}\right) + C\left(\frac{f_2}{f_1}\right)^2\right]. \quad (4)$$

According to equation (4), the dynamic pressure appearing on the left hand side of equation (4) is a function of the ratio of the two vortex shedding frequencies. Once the functional relationship appearing on the right hand side of equation (4) is determined empirically, the dynamic pressure can be determined from the ratio of the two vortex shedding frequencies respectively measured by the two vortex detectors. Since $U_1$ is determined from the vortex shedding frequency $f_1$ by equation (2) wherein the numerical value of $K_1$ is determined empirically, the density of the fluid $\rho$ is determined from the dynamic pressure determined by equation (4) and $U_1$ determined by equation (2). The volume flow rate $\dot{V}$ is given by the equation $$\dot{V} = A(U_1 + U_2), \quad (5)$$

where A is the cross section area of the flow passage 3 or 4. The mass flow rate $\dot{M}$ is determined as the product of the density of fluid and the volume flow rate.

In FIG. 3 there is illustrated a cross section of another embodiment of the multi-function flowmeter equivalent to the cross section shown in FIG. 2, which embodiment has essentially the same construction as the embodiment shown in FIG. 1 with one exception. The flap 23 has an opening 24.

In FIG. 4 there is illustrated a cross section of a further embodiment of the multi-function flowmeter having essentially the same construction as the embodiment shown in FIG. 1, which embodiment has a partially closing flap 25 in place of the fully closing flap 14 shown in FIGS. 1 and 2.

FIG. 5 illustrates a cross section of yet another embodiment of the multi-function flowmeter that has a fully closing flap 26 with a spring bias provided by a torsion coil spring 27. The cross sections shown in FIGS. 3, 4 and 5 show a few of the many different flap arrangements, wherein the flap is closed by the weight thereof or by a spring bias and opened by the dynamic pressure of the flow of fluid.

Figures 6, 7:
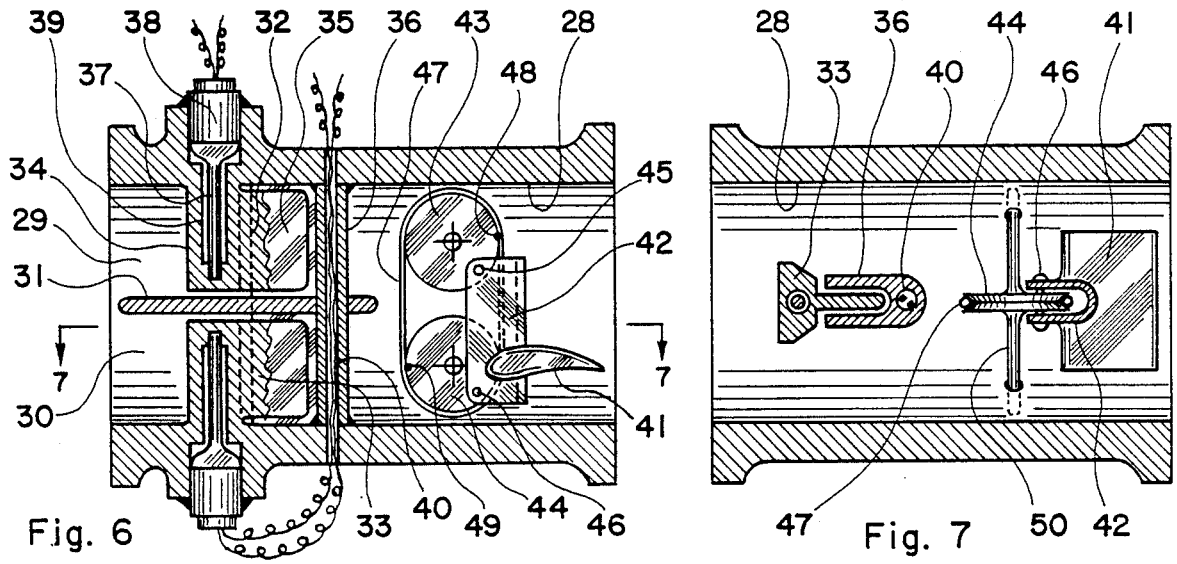
FIG. 6 illustrates a cross section of an embodiment of the present invention that comprises two vortex generator-sensor combinations and a streamlined body blocking one of the two flow passages in a spring biased or gravity biased arrangement.
FIG. 7 illustrates another cross section of the embodiment shown in FIG. 6.

In FIG. 6 there is illustrated a cross section of yet a further embodiment of the multi-function flowmeter. The upstream half of the bore 28 is divided into two flow passages 29 and 30 by a divider plate 31. The two flow passages 29 and 30 respectively include two vortex generator-sensor combinations 32 and 33 extending from two diametrically opposite portions of the wall of the bore 28 towards one another in a cantilever arrangement. The vortex generator-sensor includes a blunt leading edge 34 and a planar trailing edge 35, which planar trailing edge 35 is shielded by a pressure shield 36 having a U-shaped cross section. An elongated force receiving member 37 extending from the transducer 38 engages an oversized axial hole 39 disposed through the blunt leading edge 34 of the vortex generator-sensor combination 32, wherein the extremity of the force receiving member 37 is anchored to the blind end of the axial hole 39. The trailing edge of the pressure shield 36 includes an axial hole 40, through which the electrical wires extending from the transducer are routed. A blocking body 41 having an airfoil cross section is affixed to a planar supporting member 42 secured to the two circular discs 43 and 44 by a pair of pins 45 and 46 in a pivoting arrangement. The two discs 43 and 44 rotatably secured to the wall of the bore 28 have grooved circumferences which receive a belt 47 anchored to the two discs at the points 48 and 49, respectively.

In FIG. 7 there is illustrated another cross section of the embodiment shown in FIG. 6, which cross section taken along plane 7—7 as shown in FIG. 6, clearly shows the vortex generator-sensor 33 including a blunt leading edge and a planar trailing edge as well as the pressure shield 36 shielding the planar trailing edges of the vortex generator-sensor combinations 32 and 33. The blocking body with airfoil cross section is affixed to the planar supporting member 42 that is secured to the discs 43 and 44 with shaft 50 rotatably supported by the wall of the bore 28. The pins 45 and 46 provide a pivoting securement between the planar supporting member 42 and the two discs 43 and 44. The rotating motion of the two discs 43 and 44 are coupled by the belt 47 disposed within the circumferential grooves of the discs. The blocking body 41 with an airfoil cross section generates a lift force that shifts the blocking body 41 towards the plane occupied by the divider plate 31 as the velocity of fluid moving through the two flow passages 29 and 30 increases, which shifting motion reduces the blockage in the flow passage 30. The embodiment shown in FIGS. 6 and 7 operates on the same principles as those described in conjunction with the embodiment shown in FIGS. 1 and 2.

Figure 8:
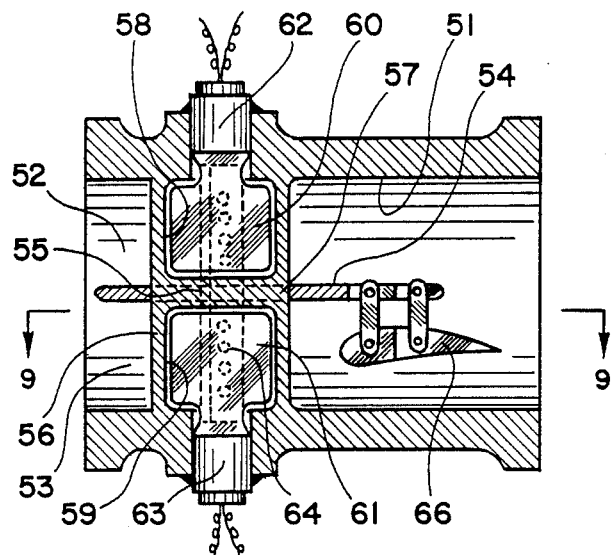
FIG. 8 illustrates a cross section of another embodiment of the present invention that comprises two vortex generator-sensor combinations and a streamlined body blocking one of the two flow passages in a spring biased or gravity biased arrangement.

In FIG. 8 there is illustrated a cross section of still another embodiment of the multi-function flowmeter comprising a bore 51 divided into two flow passages 52 and 53 by a divider plate 54. The vortex generating bluff body 55 disposed across a cross section of the bore and extending through the divider plate 54 has an upstream planar extension 56 and a downstream planar extension 57, which bluff body further includes a pair of planar cavities 58 and 59 respectively included in the two halves of the bluff body. These planar cavities 58 and 59 extending from the upstream planar extension 56 to the downstream planar extension 57 respectively include the pressure panels 60 and 61, which extend from the transducers 62 and 63, respectively. The free ends of these pressure panels 68 and 63 may be secured to the bluff body in a fixedly or simply supporting arrangement. The two sides of the bluff body 55 respectively include two sets of openings or holes 64 and 65, which openings or holes are open to the two planar cavities 58 and 59. The blocking body 66 having an airfoil cross section and partially blocking the flow passage 53 is supported by the divider plate 54 in a shiftable and nonpivotable arrangement.

Figure 9:
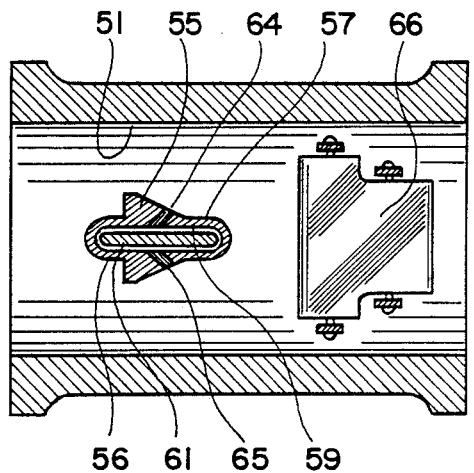
FIG. 9 illustrates another cross section of the embodiment shown in FIG. 8.

In FIG. 9 there is illustrated another cross section of the embodiment shown in FIG. 8, which cross section taken along plane 9—9 as shown in FIG. 8, shows the construction of the vortex generator-sensor combination including the bluff body 55 with upstream and downstream planar extensions 56 and 57, and the pressure panel 61 enclosed in the planar cavity 59 as well as the blocking member 66 having an airfoil cross section. The multi-function flowmeter shown in FIGS. 8 and 9 operates on the same principles as those described in conjunction with FIGS. 1 and 2.

Figure 10:
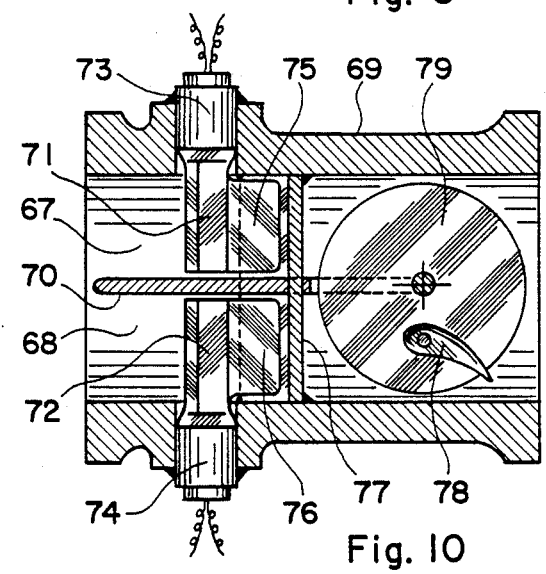
FIG. 10 illustrates a cross section of a further embodiment of the present invention that comprises two vortex generator-sensor combinations and a free pivoting body blocking one of the two flow passages in a spring biased or gravity biased arrangement.

In FIG. 10 there is illustrated a cross section of still a further embodiment of the multi-function flowmeter comprising a pair of flow passages 67 and 68 disposed through the flowmeter body 69, wherein the two flow passages 67 and 68 are separated from one another by a divider plate 70. The vortex generating bluff bodies 71 and 72 respectively extending from the transducers 73 and 74 are disposed across the two flow passages 67 and 68 in a cantilever arrangement, respectively. Of course, the free extremities of the bluff bodies 71 and 72 may be secured to the divider plate 70 in a simply or fixedly supporting arrangement. The planar trailing edges 75 and 76 are shielded by a pressure shield 77 having the same construction as the corresponding element 36 shown in FIGS. 6 and 7. The blocking body 78 having an airfoil cross section is pivotably supported by a disc 79 secured to the divider plate 70 or the flowmeter body 69 in a free-rotating relationship. The multi-function flowmeter shown in FIG. 10 operates on the same principles as those described in conjunction with FIGS. 1 and 2.

Figure 11:
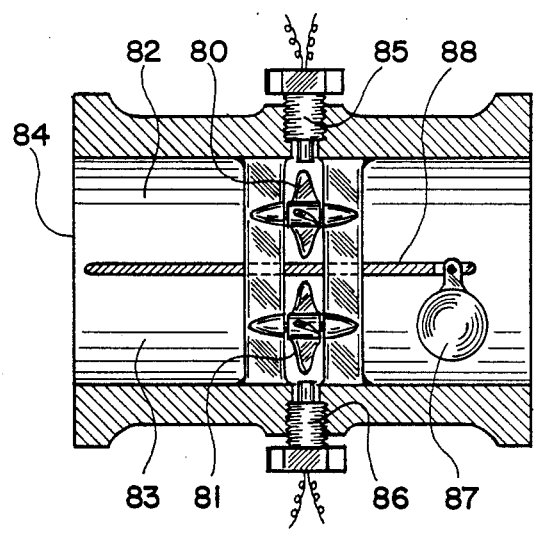
FIG. 11 illustrates a cross section of an embodiment of the present invention that comprises a pair of turbines or paddles and a blunt body blocking one of the two flow passages in a spring biased or gravity biased arrangement.

In FIG. 11 there is illustrated a cross section of an embodiment of the multi-function flowmeter comprising a pair of turbines 80 and 81 respectively measuring the velocities of the fluid flowing through two flow passages 82 and 83. The cross section of each of the two flow passages gradually changes from a semicircular cross section at the inlet end 84 of the flowmeter to a circular cross section at the section where the turbine 80 or 81 is disposed. The transducers 85 and 86 measure the rate of rotation of the two turbines, which rate of rotation is proportional to the velocity of fluid flowing thereacross. The blocking body 87 of a blunt geometry partially blocking the fluid passage 83 is supported by the divider plate 88. The multi-function flowmeter shown in FIG. 87 operates on the same principles as those described in conjunction with the equations (2), (4) and (5), wherein $f_1$ and $f_2$ now designate the rate of rotation of the turbines 80 and 81 instead of the vortex shedding frequencies. It is readily recognized that the turbines 80 and 81 may be replaced with the paddle wheels commonly employed in the fluid velocity measurement in place of the turbines.

Figure 12:
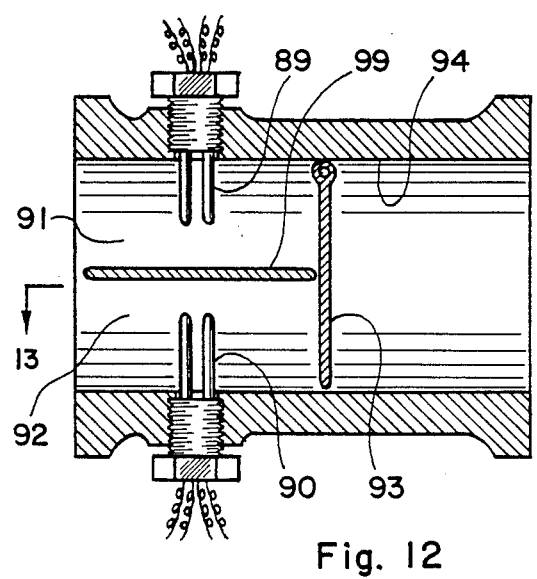
FIG. 12 illustrates a cross section of an embodiment of the present invention that comprises a pair of thermal probe combinations and a flap blocking the two flow passages at different degrees, which flap is pivotably supported in a spring biased or gravity biased arrangement.

In FIG. 12 there is illustrated a cross section of an embodiment of the multi-function flowmeter comprising two sets of thermal probe combination 89 and 90 respectively measuring the mass flow rate of fluid moving through two flow passages 90 and 91 separated from one another by a divider plate 92. The blocking body 93 comprises a circular disc flap pivotably secured to the bore 94 at the wall of the flow passage 90, which flap is spring biased or gravity biased.

Figure 13:
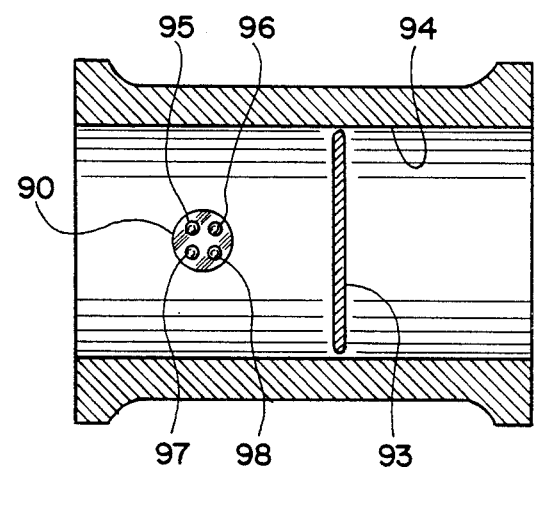
FIG. 13 illustrates another cross section of the embodiment shown in FIG. 12.

In FIG. 13 there is illustrated another cross section of the embodiment shown in FIG. 12, which cross section is taken along plane 13—13 as shown in FIG. 12. Each of the two thermal probe combinations comprises two hot probes 95 and 98, and two cold or ambient temperature probes 96 and 97, wherein the four thermal probes are positioned at the four corners of a square or rectangle having two opposite sides parallel to the direction of the fluid flow and the other two opposite sides perpendicular to the direction of fluid flow.

The mass flow rate of the fluid flowing by the quadruple thermal probe 89 or 90 is given by the equation $$\rho U_i = C \left[ \frac{(T_{HL} - T_{CL}) - (T_{HR} - T_{CR})}{(T_{HL} - T_{CL}) + (T_{HR} - T_{CR})} \right]_i, \quad (6)$$
$$i = 1 \text{ or } 2$$

where C is a coefficient of proportionality which may be a constant or a weak function of the flow velocity U, the subscripts H and C respectively stand for hot and cold probe, and the subscripts L and R respectively stand for probes disposed at one or the other side of the plane parallel to the flow direction that divides the four thermal probes into two pairs. The equation (1) can be rearranged into the form $$\frac{1}{2}\rho U_1^2 = \frac{F}{2}\left(\frac{U_2}{U_1}\right) / \left[ A + B\left(\frac{U_2}{U_1}\right) + C\left(\frac{U_2}{U_1}\right)^2 \right]. \quad (7)$$

According to equation (6), the ratio of the velocity $U_2/U_1$ is given by the equation $$\frac{U_2}{U_1} = \left[ \frac{(T_{HL} - T_{CL}) - (T_{HR} - T_{CR})}{(T_{HL} - T_{CL}) + (T_{HR} - T_{CR})} \right]_2 / \left[ \frac{(T_{HL} - T_{CL}) - (T_{HR} - T_{CR})}{(T_{HL} - T_{CL}) + (T_{HR} - T_{CR})} \right]_1. \quad (8)$$

Substitution of equation (8) into (7) determines the dynamic pressure. From the mass flow given by equation (6) and the dynamic pressure given by equation (7), the fluid density $\rho$ and the fluid velocities $U_1$ and $U_2$ are determined. Therefore, the multi-function flowmeter shown in FIG. 13 measures volume and mass flow rates as well as fluid density.

It should be mentioned that different embodiments of the blocking bodies shown in FIGS. 1 through 13 as well as many other embodiments not shown can be interchanged. In addition to spring and gravity biases providing a force that tends to increase the blockage of one of the two flow passages, other bias means such as a magnetic bias may be used in the construction of the multi-function flowmeter of the present invention.

While the principles of the present invention have now been made clear by the illustrative embodiments, it will be immediately obvious to those skilled in the art that many modifications of structures, arrangements, proportions, elements and materials which are particularly adapted to the specific working environments and operating conditions in the practice of the invention can be made without departing from those principles. It is not desired to limit the inventions to the particular illustrated embodiments shown and described and accordingly, all suitable modifications and equivalents may be resorted to falling within the scope of the inventions as defined by the claims which follow.

The embodiment of the invention in which an exclusive property or privilege is claimed, are defined as follows:

1. A multifunction flow measuring apparatus comprising in combination:
   (a) a first flow passage including a first means for measuring rate of fluid flow;
   (b) a second flow passage including a second means for measuring rate of fluid flow;
   (c) a variable position fluid dynamic target obstructing fluid flow through said second flow passage wherein degree of blockage of said second flow passage decreases as the rate of fluid flow through said apparatus increases;
   (d) means for determining volume flow rate of fluid moving through said apparatus from a combination of outputs from said first and second means for measuring rate of fluid flow; and
   (e) means for determining mass flow rate of fluid moving through said apparatus from a combination of the volume flow rate and the outputs from said first and second means for measuring rate of fluid flow.

2. The combination as set forth in claim 1 wherein the fluid density is determined as the ratio of mass flow rate to the volume of flow rate.

3. The combination as set forth in claim 1 wherein each of the first and second means for measuring rate of fluid flow comprises a vortex generator and a vortex sensor with the output providing vortex shedding frequency generally proportional to the fluid velocity.

4. The combination as set forth in claim 1 wherein each of the first and second means for measuring rate of fluid flow comprises a turbine and a rotary motion sensor with the output providing rotary speed of the turbine generally proportional to the fluid velocity.

5. A multifunction flow measuring apparatus comprising in combination:
   (a) a first flow passage including a first means for measuring rate of fluid flow;
   (b) a second flow passage including a second means for measuring rate of fluid flow;
   (c) a variable position fluid dynamic target obstructing fluid flow through said second flow passage wherein degree of blockage of said second flow passage decreases as the rate of fluid flow through said apparatus increases;
   (d) means for determining volume flow rate of fluid moving through said apparatus from an additive combination of outputs from said first and second means for measuring rate of fluid flow;
   (e) means for determining dynamic pressure of fluid flow moving through said apparatus from inequality in the output between said first and second means for measuring rate of fluid flow.

6. The combination as set forth in claim 5 wherein mass flow rate of fluid through said apparatus is determined as the ratio of the dynamic pressure to one half of the fluid velocity.

7. The combination as set forth in claim 6 wherein the fluid density is determined as the ratio of mass flow rate to the volume flow rate.

8. The combination as set forth in claim 5, wherein each of the first and second means for measuring rate of fluid comprises a vortex generator and a vortex sensor with the output providing vortex shedding frequency generally proportional to the fluid velocity.

9. The combination as set forth in claim 8 wherein mass flow rate of fluid through said apparatus is determined as the ratio of the dynamic pressure to one half of the fluid velocity.

10. The combination as set forth in claim 5 wherein each of the first and second means for measuring rate of fluid flow comprises a turbine and a rotary motion sensor with the output providing rotary speed of the turbine generally proportional to the fluid velocity.

11. The combination as set forth in claim 10 wherein mass flow rate of fluid through said apparatus is determined as the ratio of the dynamic pressure to one half of the fluid velocity.

12. A multifunction flow measuring apparatus comprising in combination:
   (a) a first flow passage including a first means for measuring rate of fluid flow;
   (b) a second flow passage including a second means for measuring rate of fluid flow;
   (c) a variable position fluid dynamic target obstructing fluid flow through said second flow passage wherein degree of blockage of said second flow passage decreases as the rate of fluid flow through said apparatus increases;
   (d) means for determining mass flow rate of fluid moving through said apparatus from a combination of outputs from said first and second means for measuring rate of fluid flow; and
   (e) means for determining volume flow rate of fluid moving through said apparatus from a combination of the mass flow rate and the outputs from said first and second means for measuring rate of fluid flow.

13. The combination as set forth in claim 10 wherein the fluid density is determined as the ratio of mass flow rate to the volume flow rate.

14. The combination as set forth in claim 10 wherein each of the first and second means for measuring rate of fluid flow comprises a thermal probe with the output generally proportional to the fluid velocity times fluid density.

* * * * *